(12) United States Patent
Kotian et al.

(10) Patent No.: US 7,123,682 B2
(45) Date of Patent: Oct. 17, 2006

(54) METHOD AND APPARATUS FOR DETERMINING FUNCTIONAL PARAMETERS IN A RADIOLOGICAL APPARATUS

(75) Inventors: François Kotian, Guyancourt (FR); Rémy Klausz, Neuilly sur Seine (FR); Yves Trousset, Palaiseau (FR); Régis Vaillant, Villebon sur Yvette (FR); Guillaume Calmon, Paris (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/721,686

(22) Filed: Nov. 25, 2003

(65) Prior Publication Data

US 2004/0252809 A1    Dec. 16, 2004

(30) Foreign Application Priority Data

Nov. 28, 2002 (FR) .................................. 02 14993
Jun. 3, 2003 (FR) .................................. 03 06676

(51) Int. Cl.
*A61B 6/02* (2006.01)

(52) U.S. Cl. .......................................... 378/21; 378/27
(58) Field of Classification Search .................... 378/4, 378/196, 197, 15, 17, 21, 22, 27, 198
See application file for complete search history.

(56) References Cited

U.S. PATENT DOCUMENTS

| | | | |
|---|---|---|---|
| 4,577,222 A | | 3/1986 | Kruger et al. |
| 5,220,588 A | * | 6/1993 | Deucher et al. ............... 378/4 |
| 5,485,502 A | * | 1/1996 | Hinton et al. ............... 378/117 |
| 6,301,324 B1 | * | 10/2001 | Pearson et al. ............... 378/4 |
| 6,442,235 B1 | | 8/2002 | Koppe et al. |
| 6,442,288 B1 | | 8/2002 | Haerer et al. |
| 2002/0085681 A1 | | 7/2002 | Jensen |
| 2002/0085682 A1 | | 7/2002 | Noegel et al. |

FOREIGN PATENT DOCUMENTS

| | | |
|---|---|---|
| WO | WO 02/079776 A | 10/2002 |
| WO | WO 01 85030 | 11/2002 |

OTHER PUBLICATIONS

Cenic et al., "Dynamic CT Measurement of Cerebral Blood Flow: A Validation Study", American Journal of Neuroradiology, Jan. 1999, vol. 20, pp. 63-73.*

Lee, Ting-Yim, "Functional CT: physiological models", Trends in Biotechnology, vol. 20, No. 8 (Suppl.), 2002.

* cited by examiner

*Primary Examiner*—Edward J. Glick
*Assistant Examiner*—Chih-Cheng Glen Kao
(74) *Attorney, Agent, or Firm*—Cantor Colburn LLP (57) ABSTRACT

A method and apparatus for determining a set of functional parameters using a fluoroscopic radiography apparatus of the type comprising an X-ray source, a detector or recorder of the radiation facing the source, the source and the detector or recorder being installed on a mobile support capable of movement with respect to a table placed between the source and the detector or recorder on which a patient with a region of interest to be X-rayed will be placed. The method comprises a) movement of the support following a given movement with respect to the table, repeated during a given time; b) acquisition by the detector or recorder of a series of images of the region of interest during movement of the support with respect to the table; c) reconstitution of a series of three-dimensional models of the region of interest, starting from a series of acquired images; and d) determination of all functional parameters.

33 Claims, 3 Drawing Sheets

METHOD AND APPARATUS FOR DETERMINING FUNCTIONAL PARAMETERS IN A RADIOLOGICAL APPARATUS

CROSS-REFERENCE TO RELATED APPLICATIONS

This application claims the priority of French Patent Application No. 02 14993 filed Nov. 28, 2002 and the priority of French Patent Application No. 03 06676 filed Jun. 3, 2003, the entire contents of both applications are hereby incorporated by reference.

BACKGROUND OF THE INVENTION

The invention relates to improvements to a radiographic imaging process and apparatus for the process. In particular, an embodiment of the invention and equivalents is an apparatus for fluoroscopic imaging and a method for monitoring the evolution of an action procedure in an angiography operating theater.

Vascular or angiography operating theaters are increasingly used for therapeutic applications. Some of these require anatomic information about vascular pathologies encountered and to be treated, and also functional information, particularly in the operational neuroradiology domain. These applications include endovascular treatments concerning cerebral vascular accidents, angioplasties of the carotid and placement of carotidian stents and intracranial stents. Knowledge of functional information is very useful for all these applications, before the surgical procedure is carried out, in order to make appropriate therapeutic decisions, and also during the procedure to be able to evaluate the effects of the treatment applied in real time, and to decide whether to stop it or to continue it if necessary.

Presently, the required functional information is obtained using magnetic resonance or calculated tomography devices, and not using an X-ray angiography or fluoroscopic device, whereas the procedure itself is carried out using an X-ray angiography device, and cannot be done with magnetic resonance or calculated tomography systems.

Means for processing can be used to deduce a three-dimensional model of the region of interest of the object, such as a patient, starting from a sequence of two-dimensional images thus acquired, in a known manner. In general, all that a medical practitioner, such as a surgeon, can use during a procedure is a single 3D model corresponding to a sequence of 2D images acquired at the beginning of the procedure.

Therefore, it is not possible to monitor the action of instruments on the anatomy of the object on which the procedure is being done (or the effects of the therapeutic action taking place on the treated tissues) on the 3D model. Thus, a medical practitioner can only obtain anatomic information from this method. Consequently, the object will firstly be examined either by magnetic resonance or by calculated tomography so as to obtain all functional information necessary to carry out the examination and the diagnostic. The object is then brought into the vascular operating theater for the therapy itself. This surgical procedure scheme is not sufficient to supply functional information that the medical practitioner might need during the procedure. At the present time, this problem is solved according to the state of the art by combining X-ray systems and magnetic resonance systems, for example, or calculated tomography systems, which lead to the combination of a vascular operating theater with a magnetic resonance or a calculated tomography unit, with an object operating table shared between the two systems. In these types of combined X-ray and magnetic resonance systems, for example, functional information is available in the magnetic resonance part while the surgical operation is done in the X-rays part. However, these systems are very complex, very expensive and occupy a lot of space (about the equivalent of two operating theaters). Consequently, in practice their use is limited to a very small number of locations.

BRIEF DESCRIPTION OF THE INVENTION

An embodiment of the invention is a radiographic, e.g., fluoroscopic, imaging method and apparatus using an apparatus comprising means for providing a source of radiation, such as an X-ray source, and means for detecting the radiation capable of forming an image, that may be installed on a mobile support capable of moving with respect to means for supporting an object. The mobile support is driven along a given movement with respect to the means for supporting the object. A sequence of images of a region of the object is processed, acquired by the means for detecting of the movement of the support with respect to the table to reconstitute a 3D model of the region. The mobile support is driven so that it carries out the movement repetitively to form a periodically refreshed 3D model of the object; and this model is presented to a user.

An embodiment of the invention is a radiographic, e.g., fluoroscopic, imaging device comprising means for providing a source of radiation, such as an X-ray source, and means for detecting the radiation and capable of forming an image that may be installed on a mobile support capable of moving with respect to means for supporting an object, such as a table. Means, such as a control unit, for or capable of driving the mobile support in movement with respect to means for support. Means for processing or capable of reconstituting and presenting a 3D model of an imaged region of the object to a user, starting from a sequence of images acquired of the region by the means for detecting radiation during a given movement of the mobile support with respect to the mean for support. The control unit is programmed to control driving movement of the mobile support so that it carries out the movement repetitively and the means for processing presents a periodically refreshed 3D model to the user.

An embodiment of the invention is a method for a radiographic apparatus, such as an X-ray apparatus, to provide a simple manner of determining anatomic information and functional information before and particularly during surgical operations. In an embodiment of the invention the method determines a set of functional parameters using a fluoroscopic radiography apparatus of the type comprising an X-ray source, means for recording facing the source, the source and the means for recording being installed on a mobile support and capable of moving with respect to a table placed between the source and means for recording, and on which an object with a region of interest to be X-rayed will be placed. The method comprises:

a) movement of the support following a given movement with respect to the table, repeated during a given time;

b) acquisition by the means for recording of a series of images of the region of interest during movement of the support with respect to the table;

c) reconstitution of a series of three-dimensional models of the region of interest, starting from a series of acquired images; and d) determination of all functional parameters associated with the region of interest, starting from the series of three-dimensional models.

An embodiment of the invention is a fluoroscopic radiography apparatus comprising an X-ray source, means for recording facing the source, the source and means for recording being placed on a mobile support and capable of moving with respect to a table placed between the source and the means for recording on which an object with a region of interest to be imaged will be positioned, a control unit comprising means for or capable of moving the support following a movement applied with respect to the table, means for processing to reconstitute a three-dimensional model of the region of interest starting from a sequence of two-dimensional images of the region of interest acquired by the means for recording during the movement applied to the support with respect to the table, the control unit and the means for processing are capable of implementing the method as described above.

BRIEF DESCRIPTION OF THE DRAWINGS

Other characteristics and advantages of the invention will appear during the following description of an embodiment of the invention and variants of it. In the appended drawings.

DETAILED DESCRIPTION OF THE INVENTION

Figure 1:
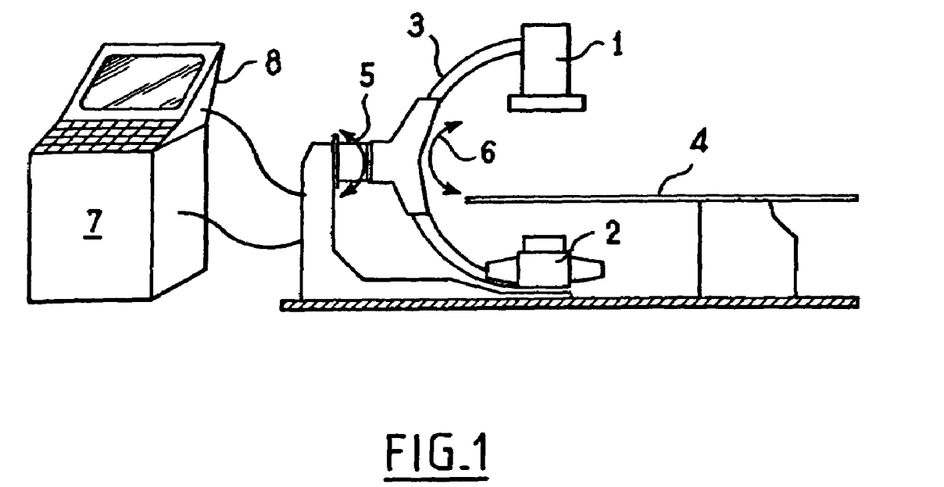
FIG. 1 illustrates an apparatus for acquisition of fluoroscopic imaging.

With reference to FIG. 1, a fluoroscopic imaging apparatus comprises means 1 for providing a source of radiation, such as an X-ray source, (radiation tubes and collimators) and means for detecting radiation 2, such as a detector (camera, sensors matrix or any other equivalent means), to detect the image formed by the irradiation. The source 1 and the detector 2 are arranged facing each other, on each side of a means for support 4, such as a table, on which there will be an object, such as a patient, with a region of interest to be imaged or X-rayed. The source 1 and the detector 2 are placed on a mobile support 3 such as a C-shaped arm and capable of rotating about a main axis of rotation corresponding approximately to the axis of the patient's body (double arrow 5 in FIG. 1). The total rotation movement about this axis is typically plus or minus 120 degrees. In general, the C-shaped arm 3 is also articulated so that it can tilt about a horizontal axis perpendicular to the patient's axis (double arrow 6 in FIG. 1). The total rotation movement is typically plus or minus 60 degrees.

A control unit 7 controls and provides means for driving the C-shaped arm 3 to make it rotate (and therefore to make the source 1 and the detector 2 also rotate) about the patient's axis and thus acquire a sequence of two-dimensional images corresponding to different directions of observation about it.

This type of apparatus has the advantage that it enables the acquisition, reconstruction and display of 3D model images in real time. It also enables refreshment of tomographic sections of a region of the anatomy in real time. For example, periodic refreshment of a 3D model enables the medical practitioner, such as a surgeon, to monitor the progress of a vascular tool during an operation in real time, or to monitor the propagation of cement that has been or is placed in a bone of the patient or to monitor the effect of ablation tools such as radio-frequency ablation tools.

Figure 2:
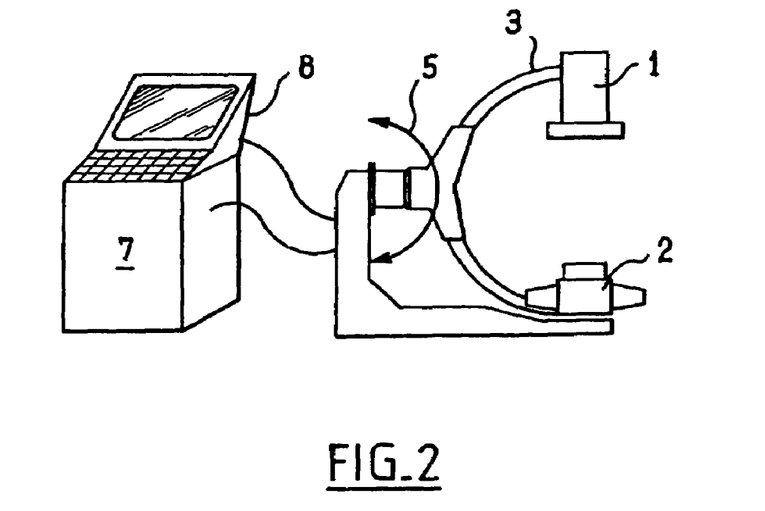
FIGS. 2 to 4 illustrate three possible acquisition movements for an apparatus according to embodiments of the invention.

FIG. 2 describes a first embodiment of an apparatus that can use a method to determine a set of functional parameters according to an embodiment of the invention, and described later. In the embodiment illustrated in FIG. 2, the acquisition apparatus comprises the same general means as the apparatus illustrated in FIG. 1. Unlike the embodiment illustrated in FIG. 1, the control unit is programmed to control driving the C-shaped arm about the patient and the table 4 along a repetitive forward-return movement, with a sequence of half-rotations over approximately 180°, alternately in one direction and then in another direction.

Each half-rotation movement enables acquisition of a complete sequence of two-dimensional images and thus allows the unit 8 to periodically reconstitute a new three-dimensional model. Thus, during a given time period during which the C-shaped arm will make a series of half-rotations about the patient and the table 4, the unit 8 will reconstitute a series of three-dimensional models, one for each half-rotation, starting from which firstly the anatomic parameters are determined by displaying at least one of the three-dimensional models on the display means seen by the surgeon, but also a series of functional parameters necessary to prepare the diagnostic (if it is done before the operation), or to evaluate progress of the operation as it is being carried out.

However, this variant embodiment may require a series of acceleration and deceleration movements, and may apply a relatively high mechanical load to the acquisition device and all acquired projections during a half-rotation that may be necessary to reconstruct the volume.

Figure 3:
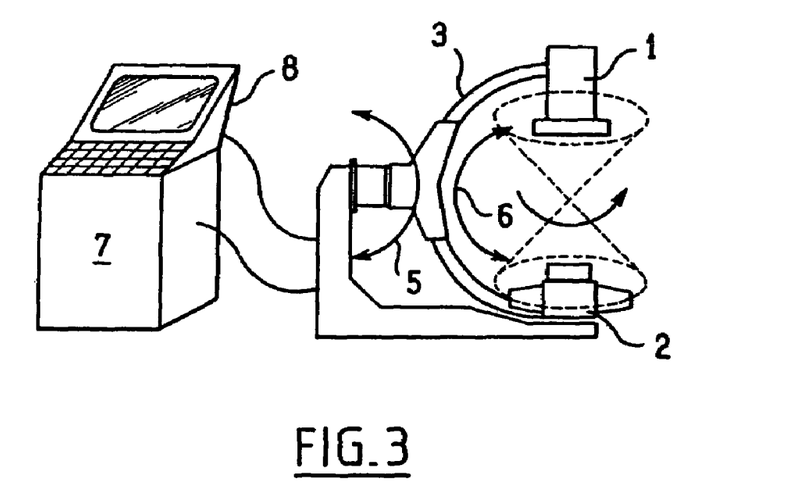

Another possible variant embodiment illustrated in FIG. 3 comprises of programming the control unit 7 so that it moves the source 1 and the detector 2 according to a movement by which the axis between the source 1 and the detector 2 rotates continuously and repetitively describing a cone of revolution. This type of acquisition movement, said to be "conical" (or circular tomography) combines rotations about a main axis that corresponds to the double arrow 5, and forward and backward movements about the other axis about which the arm 3 is articulated (double arrow 6). The processing means 8 are programmed, as described in U.S. Pat. No. 4,577,222, to reconstruct a three-dimensional model starting from a series of two-dimensional images acquired during a revolution of the source 1/detector 2 axis. This axis is driven continuously in an uninterrupted conical movement of revolution, the three-dimensional model calculated by the processing means 8 is regularly refreshed (the same is true for the two-dimensional sections of images corresponding to the orientations on which the surgeon is working).

This enables the different three-dimensional models in the series of three-dimensional models thus acquired and calculated to follow one after the other without any dead time, during a given time period. Furthermore, it enables the acquisition of two-dimensional images to start, thus enabling three-dimensional modelling at any moment in the movement cycle of the source 1/detector 2 assembly.

Figure 4:
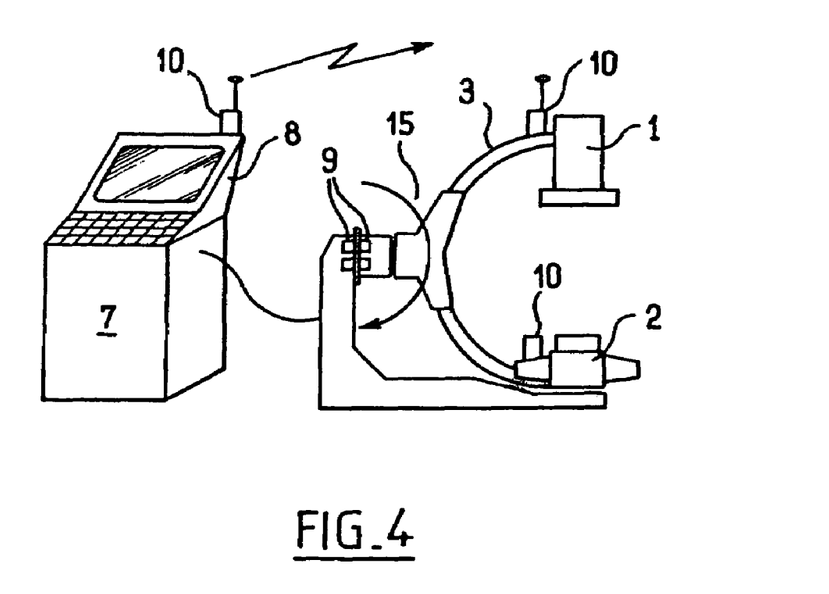

Another possible embodiment is illustrated in FIG. 4. In this embodiment, the C-shaped arm 3 is driven according to a continuous repetitive rotation movement about its main axis (arrow 15). It performs a series of complete rotations without interruption (always in the same direction of rotation) around the table 4 and the patient. To enable this type of continuous rotation movement, the electrical power supply to the arm 3 is provided (at the rotational articulation of the said arm 3 on the remainder of the support) through commutator/brush type means 9 (or rotating contacts) that avoids the need to use wire elements that would limit the rotation distance of the arm.

The control unit 7 and means for processing 8 use means 10 such as rotating contacts (bushes/commutators), optical links or radio frequency links for exchange control or acquisition data (particularly two-dimensional images acquired by the detector 2) with the source 1 and the detector 2. For example, this type of device enables the complete refreshment of the three-dimensional model or section images at a frequency of the order of 1 Hertz. As for the previous embodiment, this enables three-dimensional models in a series of three-dimensional models thus acquired and calculated to pass one after the other without any dead time during a time period of the order of 1 second, which enables a better definition of the functional parameters calculated afterwards from this series of three-dimensional models.

The means for processing unit 8 continuously memorizes a sequence of two-dimensional images on a sliding window corresponding to a number of two-dimensional images necessary to reconstruct a three-dimensional model. It continuously implements a three-dimensional reconstruction processing on this sliding window that thus enables continuous refreshment of the model at a rate that can equal the rate of acquisition of individual projections. This is a means for obtaining a series of three-dimensional models in order to optimally determine functional parameters to be determined during the surgical operation. This variant embodiment only requires a single axis of rotation.

Another possibility in one variant embodiment of this mode will be to use the rotational movement of the C-shaped arm about its other axis of rotation, for example to move the axis passing through the focal point of the source and the center of the detector, in a plane.

The embodiment illustrated in FIG. 4 also enables limited consumption of electrical power as soon as it avoids accelerations/decelerations on the C-shaped arm, and in particular it minimizes vibrations and deformations of the mechanical structure, which guarantees optimum reconstruction quality and therefore increased determination of functional parameters.

Figure 5:
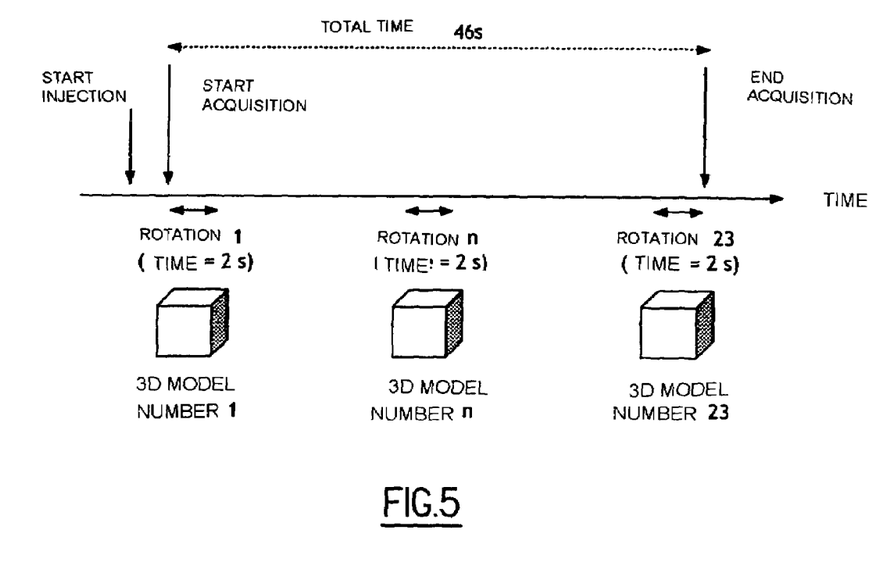
FIG. 5 is a functional diagram of a method according to an embodiment of the invention that can be used on the apparatuses of FIGS. 2 to 4.

We will now describe the method firstly to control a device like that described above, and secondly to determine a set of functional parameters. With reference to FIG. 5, the method firstly determines a series of three-dimensional models of a region of interest of a patient installed on the table 4 of the device described above, for a given time. In a second step, the method calculates functional parameters from this series of models in the form of parametric maps showing the functional parameters such as the perfusion value, the blood flow, the blood volume, the average transit time or the time before the maximum and the permeability.

The first step in the determination of a series of three-dimensional models during a given time is made by controlling a device like that described above. The three-dimensional models are calculated starting from a series of two-dimensional images. This determination of three-dimensional models was made starting from this type of acquisition, so as to determine functional information, and at a relatively high frequency to assure that it is optimized.

Typically, this optimum is of the order of one three-dimensional model per second. This frequency depends on the rotation speed of the C-shaped arm 3. For example, for a device like that used in FIG. 4 and as described above, one 180° rotation is necessary to acquire the series of two-dimensional images necessary for reconstruction of a three-dimensional model. Thus, a rotation speed of the C-shaped arm 3 equal to x° per second would theoretically enable one three-dimensional model every 180°/x seconds. For example, for a rotation speed of 90 or 60° per second, a three-dimensional model can be produced every two or three seconds respectively.

Furthermore, the total duration of an acquisition of two-dimensional images is of the order of 45 seconds, which corresponds to the time necessary to "wash" an injected bolus of a contrast product. During this 45-second period, a series of determined three-dimensional models typically comprises 15 to 45 three-dimensional models. As illustrated in FIG. 5, the moment at which the contrast products were injected is shown in the time scale, then the method controls the X-ray device for a duration of 46 seconds, rotating the C-shaped arm at a speed of 90° per second, to determine a three-dimensional model every 2 seconds. The first three-dimensional model is acquired within 2 seconds after the acquisition starts. A new three-dimensional model n is then determined every 2 seconds, until the $23^{rd}$ which is the last three-dimensional model marking the end of the acquisition. There is generally no benefit in acquiring more images, since firstly the bolus of the injected contrast product has been completely eliminated from the region of interest being considered, and secondly there is no benefit in further irradiating the patient.

In the case of a continuous acquisition, as is possible with the device according to FIG. 4, in one variant embodiment of the method, the acquisition frequency can be increased artificially by using a sliding window on the series of two-dimensional images acquired by the detection means 2. For example, the rotation n of the C-shaped arm 3 enables determination of a three-dimensional model n at time n. Similarly, rotation n+1 enables determination of a three-dimensional model n+1 corresponding to time n+1, but an intermediate three-dimensional model corresponding to time n+½ can be calculated using the second half of the series of two-dimensional images of rotation n combined with the first half of the series of two-dimensional images of rotation n+1.

Secondly, collimation systems may be used to reduce the X-ray dose sent to the patient and the medical team. From a purely application point of view, there is generally no need to acquire a complete cubic volume, and horizontal collimation strips can be used to reduce acquisition to a relatively small number of axial sections or two-dimensional images.

In a second step of the method will analyze the series of calculated previously three-dimensional models so as to determine a number of functional parameters. The theory subjacent to this step is that the grey value of a given voxel in a given three-dimensional model represents the material density through which the X-rays pass at a corresponding point in space, and for a corresponding acquisition time. When a bolus of contrast agent is injected into the blood network or into any tissue in the human body (by intravenous or intra-arterial means), the transient increase in the grey values indicates a proportional increase in the quantity of contrast product and consequently blood in the corresponding region.

In practice, in order to start this second step of the method, the work done by the operator is for example a means of defining a region of interest (ROI) at an input artery to the region of interest considered, in one of the previously determined three-dimensional models. The method according to an embodiment of the invention then defines an arterial input function (AIF). For each voxel of previously acquired and determined data, the time intensity of the signal is deconvoluted using the AIF, the residual function then obtained being called the impulse residual function (IRF). Starting from the variation profile of the IRF with time, the blood flow may be defined as being the height of the curve thus obtained (illustrating the IRF), the blood volume as being the area under the curve and the average transit time as being the length of the initial flat part of the curve. If a blood barrier is broken within a tissue, the permeability may be quantified by analyzing the exponential attenuation of the IRF.

Many authors have developed algorithms to determine the value of the different functional parameters based on the previous description. For example, refer to the article by Ting-yim Lee "Functional CT: physiological models", Trends in biotechnology—Vol. 20 No. 8—Supplement, 2002, for further information about this type of algorithm.

Figure 6:
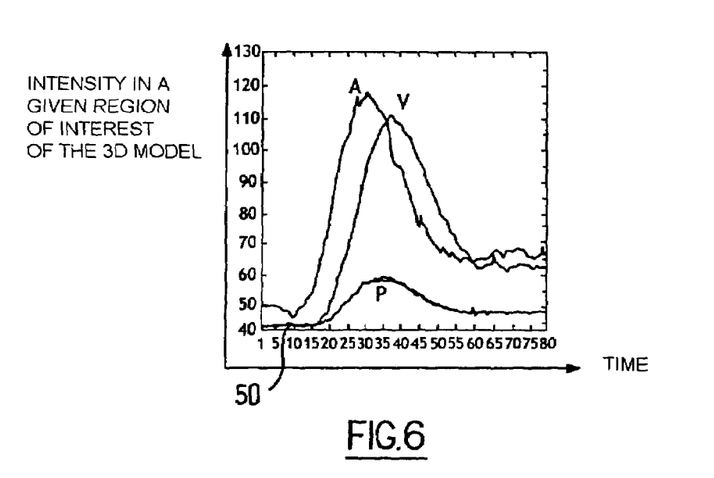
FIG. 6 is an illustration of the derived curves, so as to draw functional information from them according to an embodiment of the invention.

FIG. 6 also shows examples of IRF curves; for an artery (A), a vein (V) and a parenchymial increase (P).

The use of a method and apparatus as described above requires a much longer rotation speed than for a scanner type device used in magnetic resonance and in calculated tomography, but it has a major advantage in that the field of observation is much wider. A scanner only makes sections in its plane. Clinically, application of the method and the apparatus according to embodiments of the invention as described above applies to cerebral vascular accidents. The use of a method and an apparatus according to embodiments of the invention provides a means of accelerating the diagnostic and processing procedures for this type of accident. The operation window between the time at which the cerebral vascular accident occurs and the time at which the consequences become irreversible is of the order of a few hours. The therapy used in this case uses trombolitic agents and catheters with clamps that are inserted in the region closest to the location of the cerebral vascular accident, use of a method and an apparatus as described provides a pre-operational means of making a sort or marking of the location of the cerebral vascular accident for diagnostic, and before an operation to monitor the accident treatment as closely as possible, in a very simple manner without needing to move the patient between a conventional fluoroscopic X-ray system and a scanner system for magnetic resonance or calculated tomography.

Advantageously, but optionally, the method has at least one of the following characteristics: the support is driven along a sequence of half rotations, alternately in one direction and in the other direction around the table; the support is driven so as to apply a repetitive conical movement of revolution to the axis passing through the focal point of the source and through the center of the means for recording; the support is driven following a continuous repetitive rotation movement around the table; a sequence of two-dimensional images is continuously memorized or stored in a means for image storage, on a sliding window, corresponding to a number of images necessary for reconstitution of a three-dimensional model, and processing is applied for continuous reconstitution of a three-dimensional model on this sliding window. During the method, the method comprises the following sub-steps: choose a region of interest at a blood vessel in one of the three-dimensional models; determine an arterial input function at the chosen region of interest; deconvolute a signal with an intensity variable with time using the arterial input function, on each voxel common to three-dimensional models in the series; and determine a residual impulse function to calculate functional parameters.

Advantageously, but optionally, the apparatus has at least one of the following characteristics: the control unit is programmed to drive the support along a sequence of half-rotations alternately in one direction and in the other direction around the table; the control unit is programmed to drive the support so as to apply a repetitive conical movement of revolution to the axis passing through the focal point of the source and through the center of the means for recording; the control unit is programmed to drive the support along a repetitive continuous rotation movement around the table; the support comprises an electrical power supply with commutator/brush type means; the apparatus comprises optical connecting means through which the control unit and/or the means for processing exchange data with the source and/or means for recording; the apparatus comprises means for making a radio frequency link through which the control unit and/or the means for processing exchange data with the source and/or means for recording; the control unit and/or the means for processing exchange data with the source and/or the means for recording through brush/commutator means; and the means for processing comprise means for continuously memorizing or storing a sequence of two-dimensional images corresponding to a number of images necessary for reconstitution of a three-dimensional model on a sliding window, and also comprising means for continuously implementing a method for reconstitution of a three-dimensional model on this sliding window.

Various modifications in structure and/or function and/or steps or equivalents thereof in function and/or way and/or result may be made or proposed by one skilled in the art to the disclosed embodiments or equivalents thereof without departing from the scope and extent of the invention.

What is claimed is:

1. A radiographic imaging method using an apparatus comprising means for providing a source of radiation and means for detecting the radiation installed on a mobile support capable of movement with respect to means for supporting an object comprising:
   driving the mobile support completely along a given movement with respect to the means for supporting the object, the given movement defined by a sequence of movements that captures a sequence 2D images;
   processing the complete sequence of images of a region of the object, acquired by the means for detection during the given movement of the mobile support with respect to the means for supporting the object to reconstitute a 3D model of the region; and
   driving the mobile support so that it carries out the complete given movement repetitively to form a periodically refreshed complete 3D model of the object.

2. The method according to claim 1 wherein the mobile support is driven along a sequence of half rotations, alternately in one direction and in the other direction, around the means for supporting the object.

3. The method according to claim 2 wherein a sequence of 2D images is continuously memorized or stored, on a sliding window, corresponding to a number of images necessary for reconstitution of a 3D model, and processing is applied for continuous reconstitution of a 3D model on this sliding window.

4. The method of claim 2, wherein:
the processing a complete sequence of images to reconstitute a 3D model of the region comprises reconstituting a series of 3D models, one for each half rotation.

5. The method according to claim 1 wherein the mobile support is driven so as to apply a repetitive conical movement of revolution to an axis passing through a focal point of the source and through a center of the means for detection.

6. The method according to claim 5 wherein a sequence of 2D images is continuously memorized or stored, on a sliding window, corresponding to a number of images necessary for reconstitution of a 3D model, and processing is applied for continuous reconstitution of a 3D model on this sliding window.

7. The method according to claim 1 wherein the mobile support is driven following a continuous repetitive rotation movement, the continuous repetitive rotation defined by a series of complete rotations without interruption in the same direction, around the means for supporting the object.

8. The method according to claim 7 wherein a sequence of 2D images is continuously memorized or stored, on a sliding window, corresponding to a number of images necessary for reconstitution of a 3D model, and processing is applied for continuous reconstitution of a 3D model on this sliding window.

9. The method according to claim 1 wherein a sequence of 2D images is continuously memorized or stored, on a sliding window, corresponding to a number of images necessary for reconstitution of a 3D model, and processing is applied for continuous reconstitution of a 3D model on this sliding window.

10. The method according to claim 1 wherein the driving the mobile support is performed during an interventional procedure.

11. A radiographic imaging device comprising:
means for providing a source of radiation;
means for detecting the radiation;
the means for providing radiation and the means for detecting radiation disposed on a mobile support capable of moving with respect to means for supporting an object on which the object can be placed;
means for control capable of driving the mobile support in movement with respect to the means for supporting the object;
means for processing capable of reconstituting and presenting a 3D model of an imaged region of the object, starting from a sequence of 2D images acquired of the region by the means for detection during a given movement of the mobile support with respect to the means for supporting the object, the given movement defined by a sequence of movements that captures the sequence of 2D images;
the means for control being programmed to control driving movement of the mobile support so that it carries out the complete given movement repetitively;
the means for processing forming a periodically refreshed complete 3D model to the complete given movement repetitively carried out; and
the means for processing comprising means for continuously memorizing or storing the sequence of 2D images corresponding to a number of images necessary for reconstitution of a 3D model on a sliding window, and means for continuously implementing a method for reconstitution of the 3D model on this sliding window.

12. The apparatus according to claim 11 wherein the means for control is programmed to drive the mobile support along a sequence of half-rotations alternately in one direction and in the other direction, around the means for supporting the object.

13. The apparatus according to claim 11 wherein the means for control is programmed to drive the mobile support so as to apply a repetitive conical movement of evolution to an axis passing through a focal point of the source and through a center of the means for detecting.

14. The apparatus according to claim 11 wherein the means for control is programmed to drive the mobile support along a continuous repetitive rotation movement, the continuous repetitive rotation defined by a series of complete rotations without interruption in the same direction, around the means for supporting the object.

15. The apparatus according to claim 14 wherein the mobile support comprises an electrical power supply with a commutator/brush.

16. The apparatus according to claim 15 wherein the apparatus comprises means for optically connecting through which the means for control and/or the means for processing exchange data with the source and/or means for detecting.

17. The apparatus according to claim 15 wherein the apparatus comprises means for making a radio frequency link through which the means for control and/or the means for processing exchange data with the source and/or means for detecting.

18. The apparatus according to claim 15 wherein the means for control and/or the means for processing exchange data with the source and/or the means for detection through a brush/commutator.

19. The apparatus according to claim 14 wherein the apparatus comprises means for optically connecting through which the means for control and/or the means for processing exchange data with the source and/or means for detecting.

20. The apparatus according to claim 14 wherein the apparatus comprises means for making a radio frequency link through which the means for control and/or the means for processing exchange data with the source and/or means for detecting.

21. The apparatus according to claim 14 wherein the means for control and/or the means for processing exchange data with the source and/or the means for detection through a brush/commutator.

22. The apparatus according to claim 21 wherein the means for processing comprise:
means for continuously memorizing or storing a sequence of 2D images corresponding to a number of images necessary for reconstitution of a 3D model on a sliding window; and
means for continuously implementing a method for reconstitution of a 3D model on this sliding window.

23. The apparatus according to claim 11 wherein the means for control controls driving movement of the mobile support during an interventional procedure.

24. A method to determine a set of functional parameters using a radiography device of the type comprising means for providing a source of radiation, means for recording facing the source, the source and the means for recording being installed on a mobile support capable of moving with respect to means for supporting an object placed between the source and means for recording, and on which the object with a region of interest to be imaged will be placed, comprising:
moving the support following a given movement with respect to the means for support, the given movement defined by a sequence of movements that captures a sequence of 2D images, the given movement repeated during a given time;

acquisition by the means for recording of the complete sequence of images of the region of interest during the given movement of the mobile support with respect to the means for support;

reconstitution of a series of complete three-dimensional models of the region of interest, starting from the sequence of acquired images; and determination of functional parameters associated with the region of interest, starting from the series of complete three-dimensional models;

wherein the sequence of 2D images is continuously memorized or stored, on a sliding window, corresponding to a number of images necessary for reconstitution of a 3D model, and processing is applied for continuous reconstitution of the 3D model on this sliding window in response to the given movement repeated during the given time.

25. The method according to claim 24 wherein the determination comprises:

choosing a region of interest at a blood vessel in one of the three-dimensional models;

determining an arterial input function at the chosen region of interest;

deconvoluting a signal with an intensity variable with time using the arterial input function, on each voxel common to three-dimensional models in the series; and determining a residual impulse function to calculate functional parameters.

26. The method according to claim 25 wherein the mobile support is driven along a sequence of half rotations, alternately in one direction and in the other direction, around the means for supporting the object.

27. The method according to claim 25 wherein the mobile support is driven so as to apply a repetitive conical movement of revolution to an axis passing through a focal point of the source and through the center of the means for detection.

28. The method according to claim 24 wherein the mobile support is driven following a continuous repetitive rotation movement, the continuous repetitive rotation defined by a series of complete rotations without interruption in the same direction, around the means for supporting the object.

29. A radiography device comprising:
means for providing a source of radiation;
means for recording facing the source;

the source and means for recording being placed on a mobile support capable of moving with respect to means for supporting an object disposed between the source and the means for recording on which the object with a region of interest to be imaged will be positioned;

means for control comprising means capable of moving the mobile support following a movement applied with respect to the means for supporting the object; and means for processing;

wherein the means for control and the means for processing are capable of implementing a method according to claim 25.

30. The method according to claim 24 wherein the mobile support is driven along a sequence of half rotations, alternately in one direction and in the other direction, around the means for supporting the object.

31. The method according to claim 24 wherein the mobile support is driven so as to apply a repetitive conical movement of revolution to an axis passing through a focal point of the source and through the center of the means for detection.

32. The method according to claim 24 wherein the mobile support is driven following a continuous repetitive rotation movement, the continuous repetitive rotation defined by a series of complete rotations without interruption in the same direction, around the means for supporting the object.

33. A radiography device comprising:
means for providing a source of radiation;
means for recording facing the source;

the source and means for recording being placed on a mobile support capable of moving with respect to means for supporting an object disposed between the source and the means for recording on which the object with a region of interest to be imaged will be positioned;

means for control comprising means capable of moving the mobile support following a movement applied with respect to the means for supporting the object; and means for processing;

wherein the means for control and the means for processing are capable of implementing a method according to claim 24.

* * * * *

UNITED STATES PATENT AND TRADEMARK OFFICE
CERTIFICATE OF CORRECTION

| | | |
|---|---|---|
| PATENT NO. | : 7,123,682 B2 | |
| APPLICATION NO. | : 10/721686 | |
| DATED | : October 17, 2006 | |
| INVENTOR(S) | : Francois Kotian et al. | |

It is certified that error appears in the above-identified patent and that said Letters Patent is hereby corrected as shown below:

Column 9,
Line 58, after "3D model" insert --in response--.

Signed and Sealed this

Sixth Day of March, 2007

JON W. DUDAS
*Director of the United States Patent and Trademark Office*